(12) United States Patent
Mueller et al.

(10) Patent No.: US 10,918,328 B2
(45) Date of Patent: Feb. 16, 2021

(54) METHOD FOR DETERMINING A DEGREE OF DAMAGE TO HAIR

(71) Applicant: Henkel AG & Co. KGaA, Duesseldorf (DE)

(72) Inventors: Burkhard Mueller, Duesseldorf (DE); Torsten Lechner, Langenfeld (DE)

(73) Assignee: Henkel AG & Co. KGaA, Duesseldorf (DE)

( * ) Notice: Subject to any disclaimer, the term of this patent is extended or adjusted under 35 U.S.C. 154(b) by 0 days.

(21) Appl. No.: 16/462,418

(22) PCT Filed: Dec. 12, 2017

(86) PCT No.: PCT/EP2017/082352
§ 371 (c)(1),
(2) Date: May 20, 2019

(87) PCT Pub. No.: WO2018/114459
PCT Pub. Date: Jun. 28, 2018

(65) Prior Publication Data
US 2019/0350515 A1    Nov. 21, 2019

(30) Foreign Application Priority Data
Dec. 20, 2016    (DE) .......................... 10 2016 225 674

(51) Int. Cl.
*A61B 5/00* (2006.01)
*G01N 21/45* (2006.01)
(Continued)

(52) U.S. Cl.
CPC ............ *A61B 5/448* (2013.01); *A61B 5/0082* (2013.01); *G01N 21/45* (2013.01); *G01N 21/4738* (2013.01); *A45D 2044/007* (2013.01)

(58) Field of Classification Search
CPC A61B 5/448; A61B 5/0082; A45D 2044/007; G01N 21/45; G01N 21/25;
(Continued)

(56) References Cited

U.S. PATENT DOCUMENTS

2006/0281994 A1* 12/2006 Miyamae ............. G01N 21/359
600/473
2008/0068604 A1* 3/2008 Grossinger .......... A45D 44/005
356/328
(Continued)

FOREIGN PATENT DOCUMENTS

| EP | 2518474 A1 | 10/2012 | |
|---|---|---|---|
| WO | 03012728 A1 | 2/2003 | |
| WO | WO-2015166403 A1 * | 11/2015 | ............. G01N 21/25 |

OTHER PUBLICATIONS

EPO, International Search Report issued in International Application No. PCT/EP2017/082352, dated Mar. 20, 2018.
(Continued)

*Primary Examiner* — Christina A Riddle
(74) *Attorney, Agent, or Firm* — Lorenz & Kopf, LLP (57) ABSTRACT

A method is described for determining a degree of damage to hair, which includes: registering light which is radiated by the hair sample while a hair sample is illuminated with light; based on the registered light, determining first regions of the hair sample which reflect the light with higher interference, and second regions of the hair sample which reflect the light with lower interference; and determining a degree of damage to the hair sample based on the extents of the first regions and of the second regions.

17 Claims, 7 Drawing Sheets

(51) Int. Cl.
  *G01N 21/47* (2006.01)
  *A45D 44/00* (2006.01)
(58) Field of Classification Search
  CPC .... G01N 21/47; G01N 21/4738; G01N 21/55;
       G01N 33/4833; G01N 2021/4711; G01N
       2021/4735; G01N 2201/12; G01J 3/0264;
       G01J 3/463; G01J 3/504; G01J 3/46;
       G01J 3/50
  USPC ............ 356/229, 237.1, 238.1–238.3,
       356/239.1–239.8, 237.2–237.6, 242.1,
       356/244, 600, 601, 609, 625, 626, 630,
       356/429–431; 132/212, 221; 600/407,
       600/476, 477
  See application file for complete search history.

(56) References Cited

U.S. PATENT DOCUMENTS

| | | | | |
|---|---|---|---|---|
| 2012/0320191 A1* | 12/2012 | Meschkat | .............. | G01N 21/84 348/135 |
| 2013/0287715 A1 | 10/2013 | Juesten et al. | | |
| 2016/0007908 A1* | 1/2016 | Guo | .................... | A61B 5/6838 348/77 |
| 2016/0249849 A1* | 9/2016 | Mihara | ................ | A61B 5/0051 600/306 |

OTHER PUBLICATIONS

Manuel Gamez-Garcia, et al.: "The effects of lipid penetration and removal from subsurface microcavities and cracks at the human cuticle sheath", J. Cosmet. Sci, 60, Apr. 1, 2009, pp. 85-95, XP055458042, Retrieved from the Internet: URL: http://www.nononsensecosmethic.org/wp-content/uploads/2015/04/The-effects-of-lipid-penetration-and-removal-from-subsurface-Microcavities.pdf, retrieved on Mar. 9, 2018.

Manuel Gamez-Garcia, et al.: "Patterns of light interference produced by damaged cuticle cells in human hair", Journal of the Society of Cosmetic Chemists, vol. 58, No. 4, 269-282, Jan. 1, 2007, Abstract, XP055458010, Retrieved from the Internet: URL: http://journal.scconline.org/abstracts /cc2007/cc058n04/p00269-p00282.html, retrieved on Mar. 9, 2018.

Sangyun Lee, et al.: "Quantitative Morphological and Biochemical Studies on Human Downy Hairs using 3-D Quantitative Phase Imaging", May 15, 2015, XP055458012, Retrieved from the Internet: URL: https://arxiv.org/ftp/arxiv/papers/1505/1505.04231.pdf.

* cited by examiner

FIG 7

METHOD FOR DETERMINING A DEGREE OF DAMAGE TO HAIR

CROSS-REFERENCE TO RELATED APPLICATION

This application is a U.S. National-Stage entry under 35 U.S.C. § 371 based on International Application No. PCT/EP2017/082352, filed Dec. 12, 2017, which was published under PCT Article 21(2) and which claims priority to Germany Application No. 10 2016 225 674.2, filed Dec. 20, 2016, which are all hereby incorporated in their entirety by reference.

TECHNICAL FIELD

The present disclosure relates to a method for determining a degree of damage to hair.

BACKGROUND

When treating hair with cosmetic products, an effect of the product, for example an intensity of color, is strongly dependent on the degree of damage of the hair. Thus, the determination of damage to the hair is of great importance. Furthermore, it may be desirable to counteract damage to the hair, wherein here again, a determination of the degree of damage is useful in being able to select a suitable care product. Correspondingly, opportunities for determining the degree of damage to the hair that are effective and comfortable for the user are desirable.

BRIEF SUMMARY

In accordance with various exemplary embodiments, a method for determining a degree of damage to hair is described, which includes: registering light which is radiated by the hair sample while a hair sample is illuminated with light; based on the registered light, determining first regions of the hair sample which reflect the light with higher interference, and second regions of the hair sample which reflect the light with lower interference; and determining a degree of damage to the hair sample based on the extents of the first regions and of the second regions.

BRIEF DESCRIPTION OF THE DRAWINGS

The present disclosure will hereinafter be described in conjunction with the following drawing Figs., wherein like numerals denote like elements, and.

DETAILED DESCRIPTION

The following detailed description is merely exemplary in nature and is not intended to limit the disclosure or the application and uses of the subject matter as described herein. Furthermore, there is no intention to be bound by any theory presented in the preceding background or the following detailed description.

In the detailed description below, reference will be made to the accompanying drawings which form a part of the present disclosure and which show specific embodiments for illustration purposes, in which the present disclosure can be implemented. It should be understood that other embodiments may be used and structural or logical modifications may be made without deviating from the scope of protection of the present disclosure. It should be understood that the features in the various exemplary embodiments described herein may be combined together, unless specifically indicated otherwise. The following detailed description should therefore not be construed in a limiting manner, and the scope of the present disclosure is defined in the accompanying claims.

Figure 1:
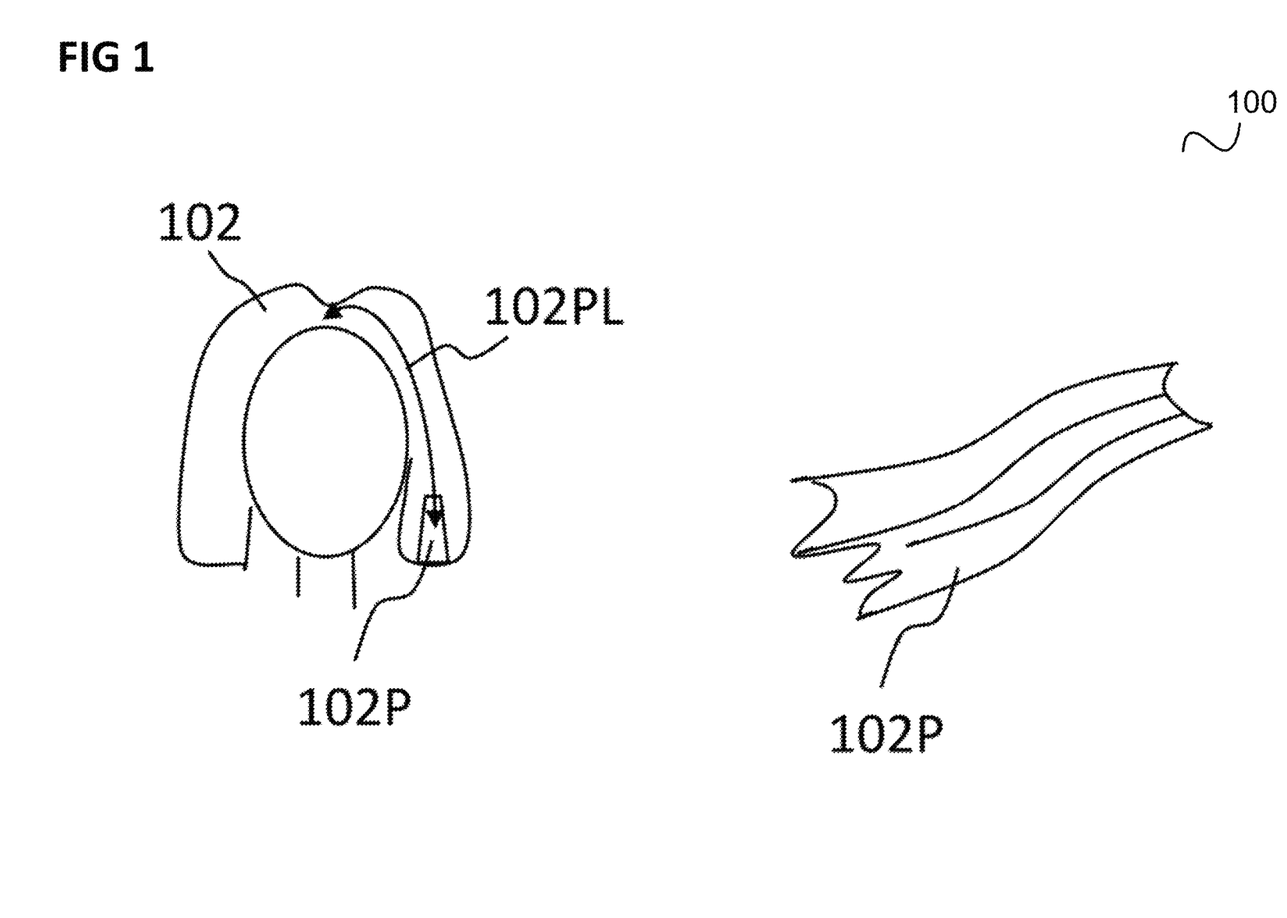
FIG. 1 illustrates taking a hair sample.

FIG. 1 illustrates taking a hair sample.

In accordance with various exemplary embodiments, a hair sample 102P is removed in order to determine a degree of damage to hair 102 of a user. The hair sample 102P may, for example, be removed at 102PL from the hair on the user's head and may be a single hair or several hairs.

Determination of the degree of damage to hair 102 from a user may also be carried out without removing a sample of hair 102P, by carrying it out directly on the user's head.

Exemplary embodiments will now be described in which damage to hair will be assessed using interference reflection microscopy.

Very fine hair structures can be investigated using interference reflection microscopy. Interference microscopy is based on the formation of interference which occurs when light is reflected at the upper and lower boundaries of a structure and reflected light from both of the boundaries interferes. This gives rise to interference patterns which can be observed, providing information regarding the thickness of the structure. The interference colors which are produced enable structural measurements to be carried out in the sub-20 nm region. By observing the interference colors through an optical microscope, these structural measurements can be appropriately assigned to microscopically detectable structures.

In accordance with various embodiments, this is applied to the cuticle of a hair.

Figure 2:
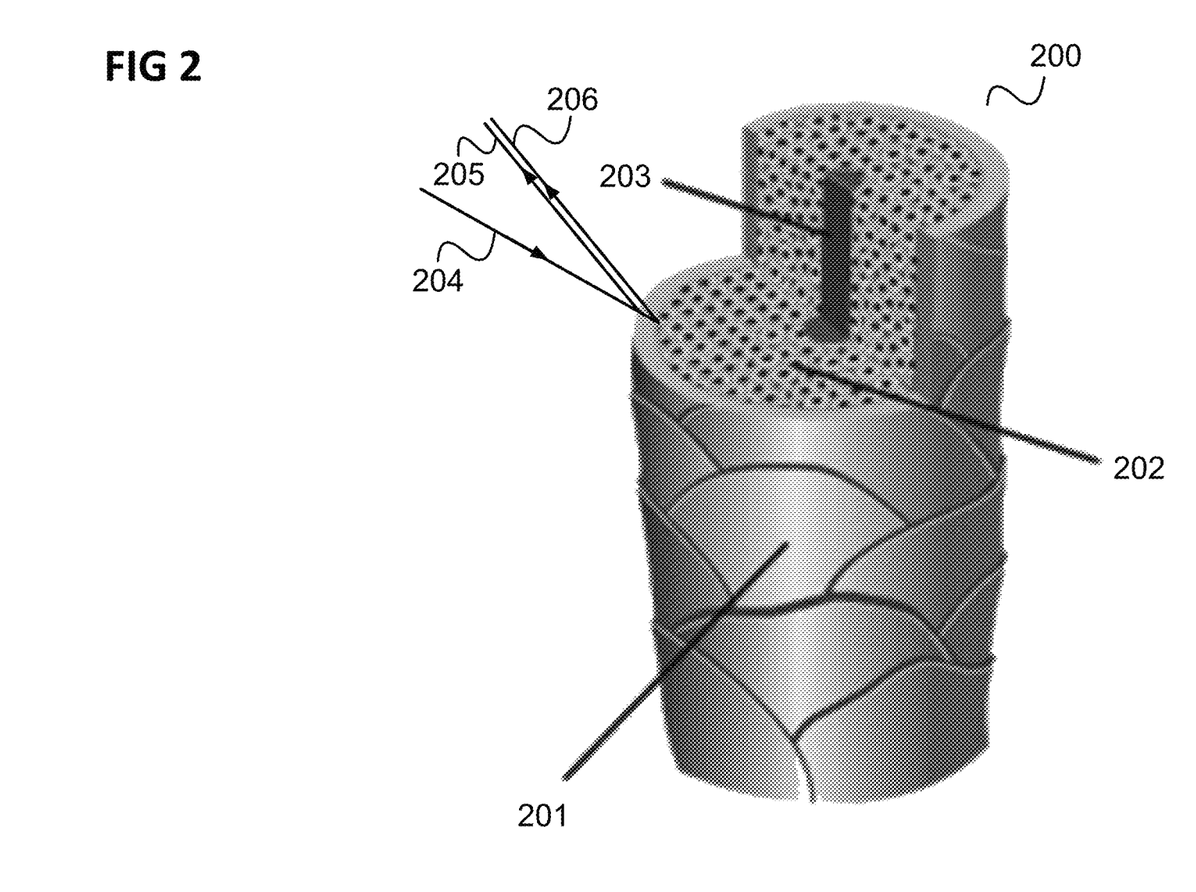
FIG. 2 shows the construction of a hair.

FIG. 2 shows the construction of a hair 200.

The hair has a cuticle 201, a cortex 202 and medulla 203.

If the hair is irradiated with light 204, then a portion of the light is reflected at the outer surface of the cuticle 201 and a portion is reflected at the boundary between the cuticle 201 and cortex 202 (in particular when the cuticle 201 has become lifted or detached from the cortex 202, which typically corresponds to damage to the hair). The reflected portions 205, 206 interfere and form an interference pattern.

Figure 3:
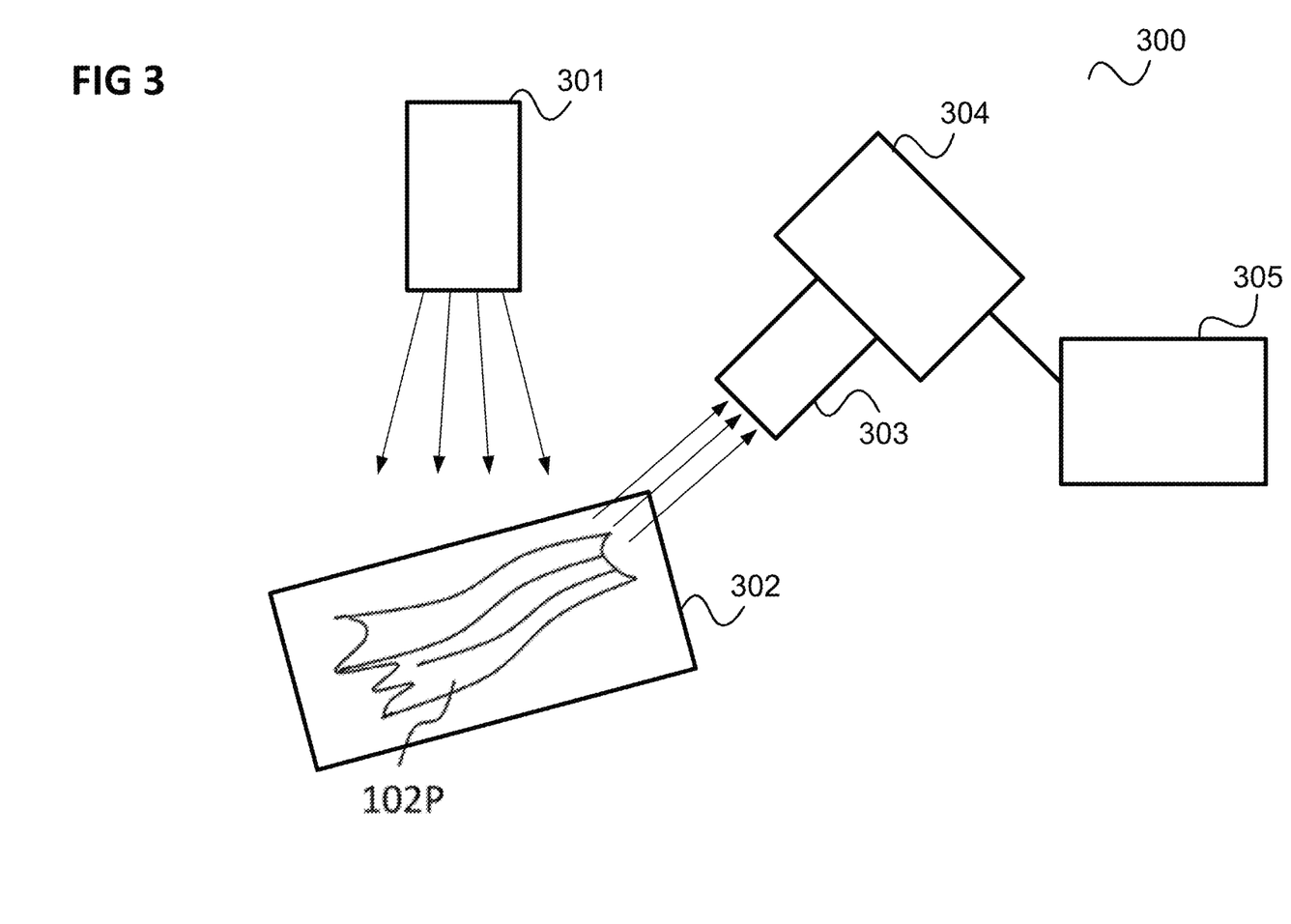
FIG. 3 shows a scheme for determining a degree of damage to hair.

FIG. 3 shows a scheme 300 for determining a degree of damage to hair.

The scheme includes a light source 301 which is conFIG.d configured in a manner such that it irradiates a hair sample 102P which, for example, includes a plurality of hairs (i.e. hair fibres) with white light.

The hair sample 102P is, for example, disposed in or on a support 302. A camera 304, which is coupled to an interference microscope 303, is directed onto the hair sample 102P and receives light reflected from the hair sample 102P; it takes photographs of one or more hair fibres.

The magnification factor of the microscope is, for example, in the range from about 10 to about 1000, for example in the range from about 200 to about 400, and is adjustable, for example.

The scheme 300 furthermore includes a data processing device 305 which is configured in a manner such that it can evaluate the photographs and determine damage (for example a degree of damage) on the photographs.

The data processing device 305, for example for each of one or more photographs, determines the type and/or number of interference patterns for the hair by employing image analysis software, compares it with a calibration model produced in an identical manner, and therefore determines a degree of damage of the hair. When a plurality of photographs has been taken, then the data processing device 305 may, for example, produce a mean for the degrees of damage determined for the photographs.

The interference microscopy 303, the camera 304, the data processing device 305 and optionally also the light source 301 and the support 302 may be formed by a smart phone which is equipped with a microscope lens for smart phones which is also suitable for interference microscopy. Alternatively, the interference microscope 303, the camera 304, the data processing device 305 and optionally also the light source 301 and the support 302 may be produced by a MILAN-enabled media player, such as the iPod Touch, or a tablet.

As an example, hairs can be imaged at 350× magnification by employing a portable electronic device (such as a smart phone, a tablet, etc) with a microscope attachment (such as a Scrona μpeek, for example) in combination with an interference slider (such as that offered by Hirox Ltd).

The interference colors are observed by looking through an optical microscope, and therefore these structural measurements can be allocated to the microscopically detectable structures. Oil immersion and an anti-glare lens may be used in order to minimize contrast-reducing reflections at the surfaces of the glass (for example of the support 302). A central screen may be disposed in the path of illumination in order to block reflections form the central region of the lens.

Figure 4:
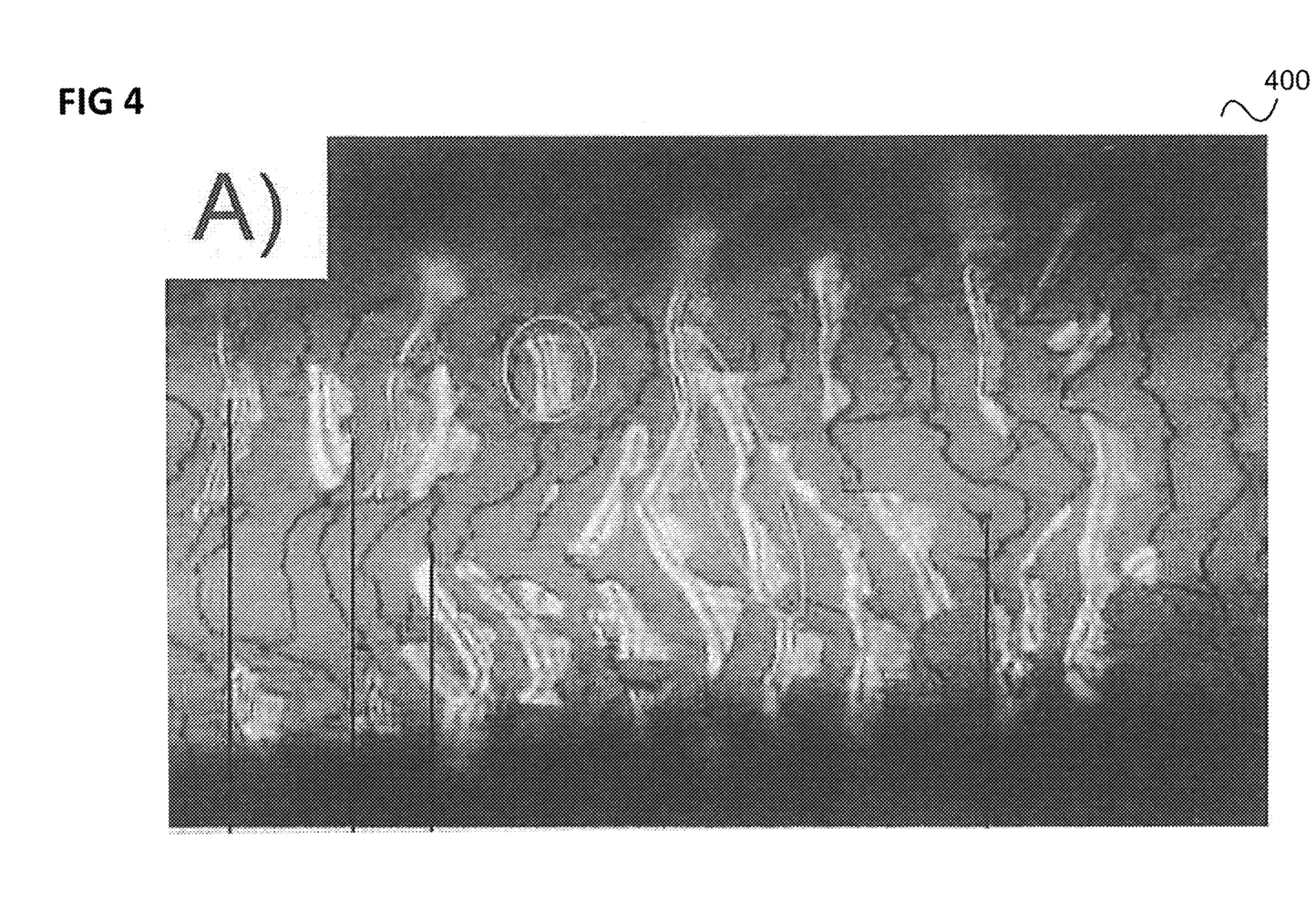
FIG. 4 shows an example of an image of an individual hair which is recorded in accordance with one exemplary embodiment.

FIG. 4 shows an example of an image 400 of an individual hair which, for example, is registered (i.e. recorded) by employing the camera 304.

The image 400 may be recorded in color by the camera 304 and converted into a black and white version by the data processing device 305, as can be seen in FIG. 4. Alternatively, the camera 304 could record the image 400 in black and white.

The data processing device can determine the proportional area of bright areas in the image 400, for example with an image processing computer program installed on the data processing device. In this regard, a brightness threshold may be predetermined and the data processing device detects areas with a brightness lower than the brightness threshold as dark, and areas with the brightness higher than the brightness threshold as bright. The brightness threshold is, for example, defined with reference to the brightness of the dark regions of the photograph (for example as a factor of the brightness of the dark regions).

The proportional area of the interfering hair structures, i.e. the proportion of bright regions with respect to the total area of the hair in the photograph, is between about 1% and about 50%, for example, for example between about 5% and about 30%.

The data processing device can then calculate the degree of damage from the determined proportional area of bright areas, for example with the aid of a table, which allocates degrees of damage to the proportional area ranges.

For calibration (i.e. in order to draw up such a table, for example), as an example, hair from hair samples is stretched through a predetermined tensile elongation of the hair and is damaged thereby. As an example, the degree of stretching for all hair samples is kept constant and the number of stretching/relaxation cycles is varied in order to obtain different degrees of damage, for example in the range of 1 to about 1000 stretching/relaxation cycle(s). The resulting damage to the hair (depending on the number of stretching/relaxation cycles) is examined using interference microscopy as described above and analysed using image processing software which determines the proportional area of the interfering surfaces of the hair (which show up as significantly brighter than the remainder of the hair). The determined proportional areas are a measure of the degree of damage to the hair and can be allocated a degree of damage (which, for example, corresponds to ranges of numbers of stretching/relaxation cycles), in order to calibrate the data processing device.

As an example, in order to carry out calibration, hair is damaged by stretching it by about 20% and then relaxing it for about 1 second at room temperature. This process is carried out multiple times. As an example, for every 10 hairs, the following numbers of stretches are carried out:

1
3
10
30
100
300
1000

Next, all of the hairs from one group (i.e. the hairs which were subjected to the same number of stretches) were put under the microscope and the proportion of bright (interfering) areas was determined using image analysis software; subsequently, the mean of the hairs in the group was determined. In this manner, proportional areas could be allocated to the damage to the hair which had occurred.

Figure 5:
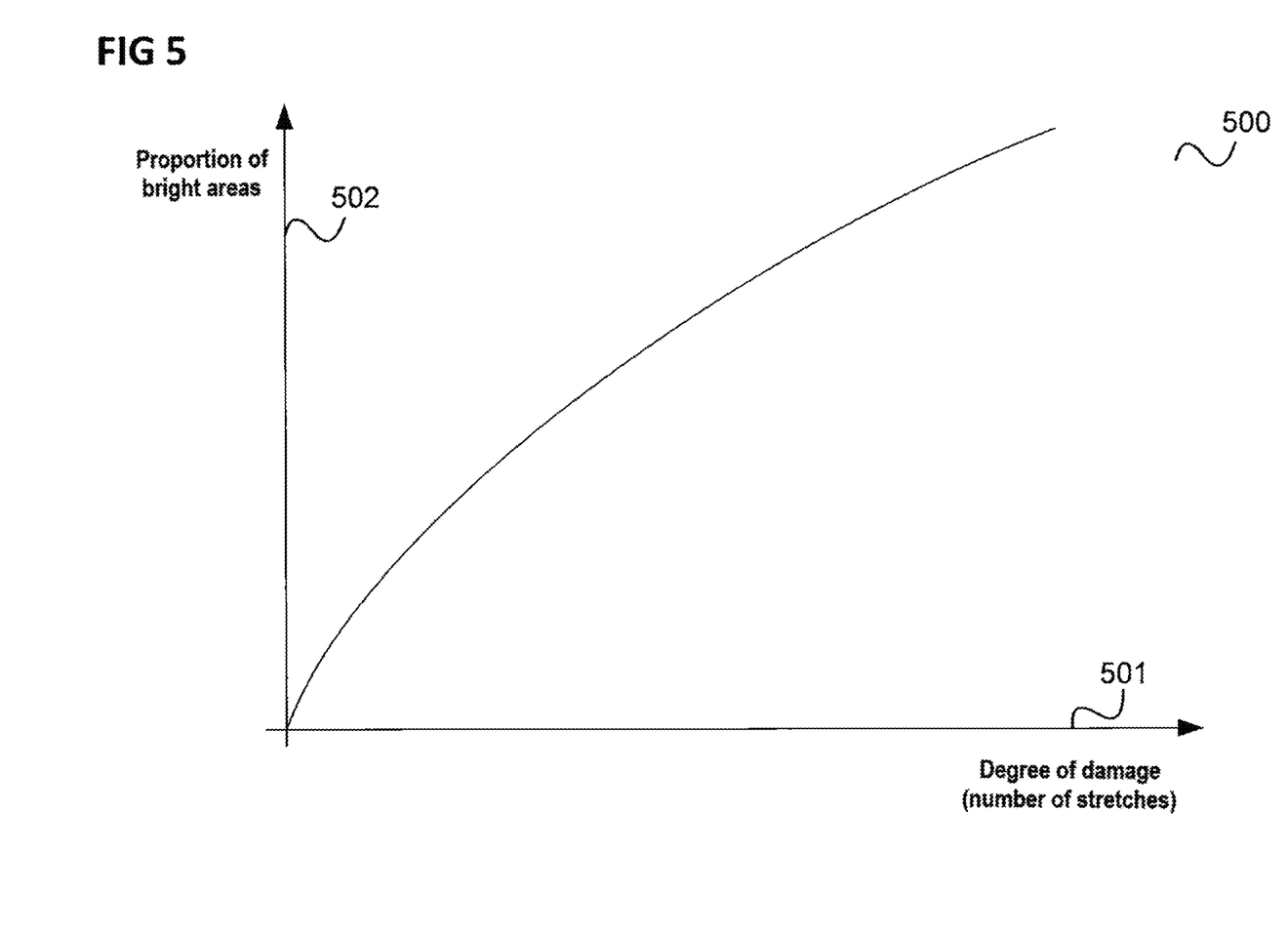
FIG. 5 shows a graph which represents an example of the relationship between a degree of damage to the hair and the proportion of light areas in the interference image.

A degree of damage—expressed as the number of stretches at about 20%—can be determined for each fraction of bright areas by interpolation of the proportion of bright areas so that, for example, a graph is obtained such as that shown in FIG. 5.

FIG. 5 shows a graph 501 which represents an example of the relationship between a degree of damage to hair, increasing from left to right along the x axis 502, and the proportion of bright areas in the interference image, increasing from bottom to top along the y axis 503.

The degree of damage is assigned stages of damage as shown, for example, in Table 1.

TABLE 1

| Degree of damage, as number of stretches | Stage of damage |
| --- | --- |
| 0 to 3 | Low |
| 4 to 10 | Medium |
| 11 to 100 | Severe |
| More than 100 | Very severe |

As an example, 2 to about 20 stages of damage may be defined, for example 2 to 4.

The damage to hair of test hair (i.e. hair the degree of damage of which is to be determined) is determined in accordance with the calibration curve as shown by way of example in FIG. 5 and stored in the form of a table, for example (online, for example). From the damage to the hair (for example for each stage of damage in accordance with Table 1), the data processing device 205 outputs a product recommendation, for example based on empirical values, in turn based on empirical tables, for example, and proposes them to the user. If the data processing device 305 is a smart phone or tablet, the smart phone or tablet shows the user a product recommendation on its display, for example. Alternatively, in the case in which the data processing device 305 is a smart phone or tablet, the user could be told the product recommendation by employing a speaker.

As an example, the data processing device 305 will recommend products with a greater conditioning power for severely damaged hair, and products with moderate or lesser conditioning power for less severely damaged hair. The conditioning power may be delivered by known care products such as quaternary nitrogen compounds (for example hexadecyltrimethylammonium chloride), cationic polymers (for example those with the INCI (International Nomenclature of Cosmetic Ingredients) name poly quaternium-10) or silicones (for example as named by the INCI). In particular, dicarboxylic acids may also be suitable in this regard.

The determination of the degree of damage and the associated product recommendation is, for example, carried out automatically by the data processing device 305, for example by software which is installed on the data processing device, for example a smart phone, a tablet or a PC.

The data processing device 305 determines the product to be recommended, for example, based on a database which contains a product recommendation for each degree of damage. An example is shown in Table 2.

TABLE 2

| Stage of damage | Product recommendation |
| --- | --- |
| Low | Product 1 for gentle hair care, containing hexadecyltrimethylammonium chloride (0.2%) |
| Moderate | Product 2 for moderate hair care, containing hexadecyltrimethylammonium chloride (0.2%) + polyquaternium-10 (0.5%) |
| Severe | Product 3 for intense hair care, containing hexadecyltrimethylammonium chloride (0.2%) + polyquaternium-10 (0.5%) + dimethicone (1%) |
| Very severe | Product 4 for very intense hair care, containing hexadecyltrimethylammonium chloride (0.2%) + polyquaternium-10 (0.5%) + dimethicone (1%) + succinic acid (1%) |

Figure 6:
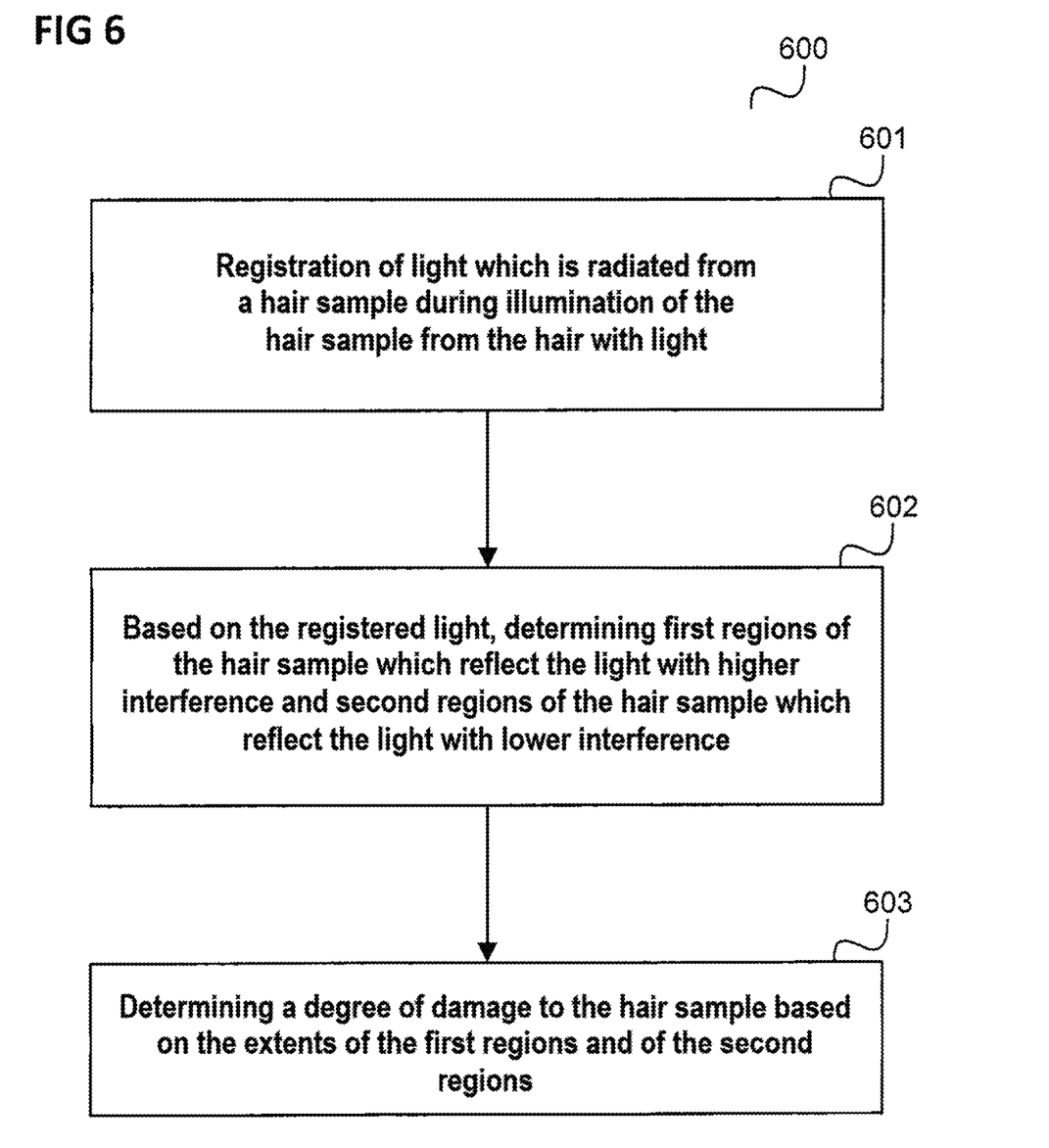
FIG. 6 shows a flow chart which illustrates a method for determining a degree of damage to hair.

In summary, in accordance with various embodiments, a method for determining a degree of damage to hair is provided which is as illustrated in FIG. 6.

FIG. 6 shows a flow chart 600.

In 601, during illumination of a hair sample of hair with light, light which is radiated by the hair sample is registered.

In 602, based on the registered light, first regions of the hair sample are determined which reflect the light with higher interference and second regions of the hair sample are determined which reflect the light with lower interference.

In 603, a degree of damage of the hair sample is determined, based on the extents of the first regions and of the second regions (for example based on the total extent of the first and/or the total extent of the second regions, for example based on the proportional area of the total extent of the first regions over the total surface area of the hair sample or based on the ratio of the total extent of the first regions to the total extent of the second regions).

In other words, in accordance with various embodiments, a method for the determination (and subsequent reduction, for example) of damage to hair is provided, which is based on an analysis with the aid of patterns recorded on the surface of one or more hairs with the aid of interference microscopy. In this regard, the severity of damage to a hair (or a plurality of hairs) is determined, which establishes how large the regions of the hair are in which high interference occurs (for example in relation to the regions or to the total region of the hair being observed). A high interference may arise, for example, when the cuticle lifts from the cortex, which is indicative of damage to the hair. The hair is, for example, illuminated with white light (for example daylight) and the occurrence of interference in the various regions of the hair is investigated in reflected light.

It should be noted that the determination of the damage based on the ratio of the extent of the first regions to the total area can also be seen as being based on the extent of the second regions, because the extent of the first regions becomes smaller as the second regions become larger (the sum of the extents of the first regions and the extents of the second regions is, for example, the total area, if appropriate plus regions which are associated with neither with the first regions nor the second regions, for example regions with a medium interference).

The method in accordance with FIG. 6 may be carried out with a portable electronic device such as a smart phone, for example, and thus constitutes a simple opportunity for the user to determine damage to the hair.

Figure 7:
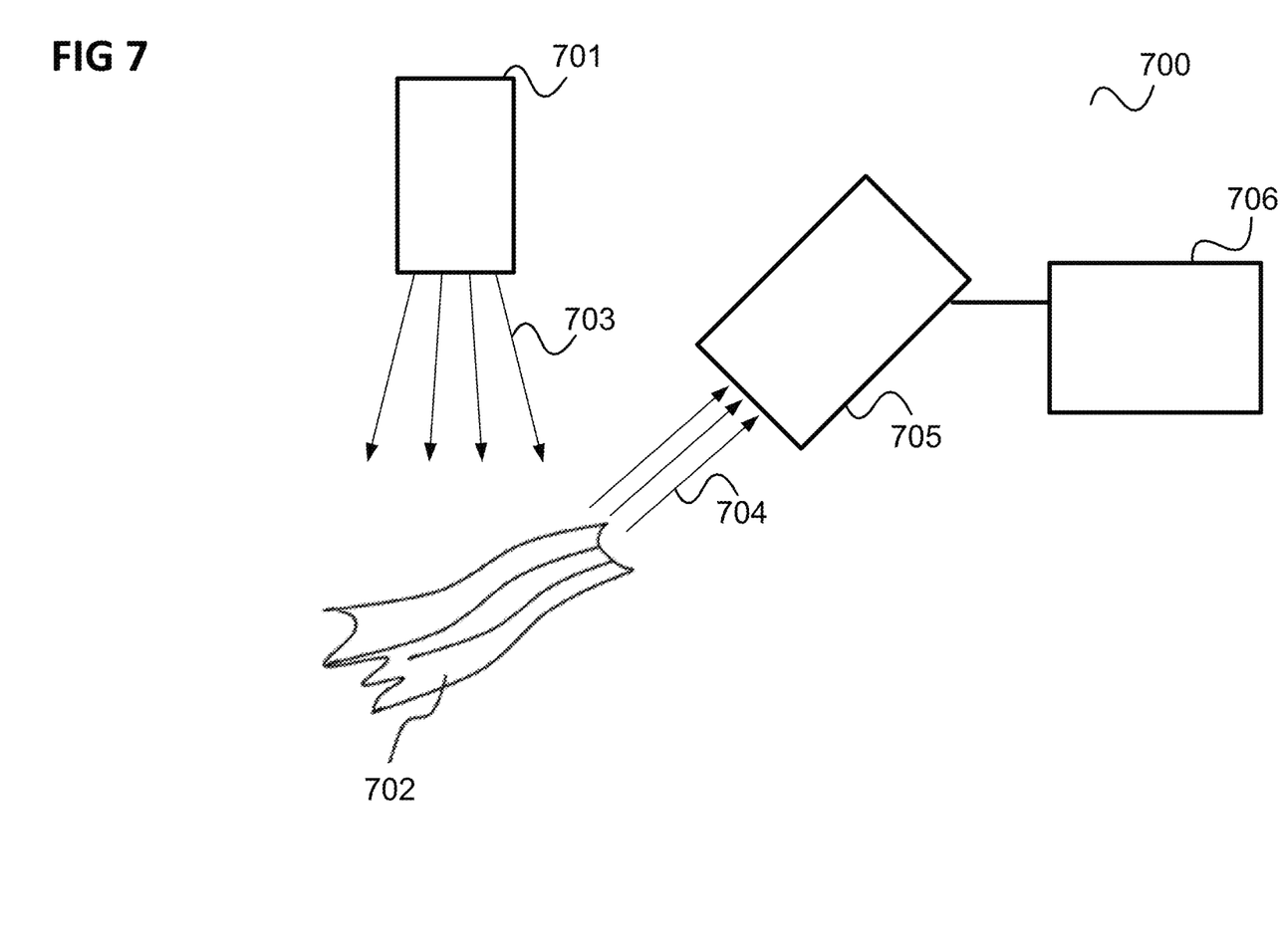
FIG. 7 shows a scheme for determining a degree of damage to hair.

The method in accordance with FIG. 6 is, for example, carried out by a scheme as illustrated in FIG. 7.

FIG. 7 shows a scheme 700 for determining a degree of damage to hair.

The scheme 700 includes a lamp 701 which is configured to illuminate a hair sample 702 of the hair with light 703, and a light registering device 705 which is configured so as to register light 704 which is radiated from the hair sample.

Furthermore, the scheme includes a data processing device 706 which is configured to determine, based on the registered light, first regions of the hair sample which reflect the light with higher interference and second regions of the hair sample which reflect the light with lower interference, and to determine a degree of damage of the hair sample based on the extent of the first regions and the extent of the second regions.

It should be noted that exemplary embodiments which are described in connection with the method for determining a degree of damage to hair are analogously applicable to the method and scheme for determining a degree of damage to hair, and vice versa.

Based on the determined degree of damage, an objectively determined recommendation may furthermore be provided to the consumer (for example automatically via a smart phone) as to which products are suitable for the hair, for example to compensate for the ascertained damage.

Exemplary embodiments will be described below:

Exemplary embodiment 1 is a method for determining a degree of damage to hair as illustrated in FIG. 6.

Exemplary embodiment 2 is a method in accordance with exemplary embodiment 1, wherein the light is registered using an interference microscope.

Exemplary embodiment 3 is a method in accordance with exemplary embodiment 1 or 2, wherein the registration of the light includes recording a photograph of the hair sample.

Exemplary embodiment 4 is a method in accordance with one of exemplary embodiments 1 to 3, wherein the determination of the first regions and the determination of the second regions includes determining brighter regions and darker regions of the photograph.

Exemplary embodiment 5 is a method in accordance with one of exemplary embodiments 1 to 4, wherein the determination of the first regions includes determining regions of the photograph with a brightness that is higher than a predetermined threshold or greater than or equal to a predetermined threshold.

Exemplary embodiment 6 is a method in accordance with exemplary embodiment 5, wherein the determination of the second regions includes the determination of regions of the photograph with a brightness that is less than or equal to the predetermined threshold or less than the predetermined threshold.

Exemplary embodiment 7 is a method in accordance with one of exemplary embodiments 1 to 6, including determination of the degree of damage for a plurality of hair samples and determining, as the degree of damage to the hair, a mean degree of damage for the determined degrees of damage.

Exemplary embodiment 8 is a method in accordance with one of exemplary embodiments 1 to 7, wherein the hair sample includes one or more hairs.

Exemplary embodiment 9 is a method in accordance with one of exemplary embodiments 1 to 8, wherein results from comparative measurements are used for the determination of the degree of damage to the hair.

Exemplary embodiment 10 is a method in accordance with one of exemplary embodiments 1 to 9, wherein the degree of damage is determined on the basis of calibration data which represent a previously determined allocation of proportions from regions with higher interference in hair samples to degrees of damage.

Exemplary embodiment 11 is a method in accordance with exemplary embodiment 10, including determining the calibration data based on hair samples with known damage.

Exemplary embodiment 12 is a method in accordance with exemplary embodiment 11, including producing known damage in the hair samples by employing predetermined stretching of the hairs of the hair samples.

Exemplary embodiment 13 is a method in accordance with one of exemplary embodiments 1 to 12, including illuminating the hair sample with white light.

Exemplary embodiment 14 is a method in accordance with one of exemplary embodiments 1 to 13, further including selecting a user-specific means with the aid of the determined degree of damage.

Exemplary embodiment 15 is a method in accordance with exemplary embodiment 14, further including displaying the selected user-specific means.

Exemplary embodiment 16 is a scheme for determining a degree of damage to hair, as illustrated in FIG. 7.

In a further embodiment, the present disclosure includes a method for determining an individual hair treatment recommendation, exemplified by the steps of:
a) recording interference patterns for a plurality of samples of hair which have been damaged to varying extents;
b) establishing a calibration model which produces a correlation between interference patterns and the degree of damage;
c) recording interference patterns of the hair from an individual;
d) determining a degree of damage to the hair of that individual with the aid of the calibration model;
e) outputting an individual recommendation regarding the treatment of the hair of the individual which is dependent upon the determined degree of damage.

For example, the individual treatment recommendation includes a recommendation of hair care products. It is optional for the method for determining an individual hair treatment recommendation to further include a step for initiating ordering of a recommended hair care product which is commercially available. For example, the individual treatment recommendation includes advising or discouraging the individual to use/from using hair care products which the individual identifies with the aid of QR codes, NFC chips, barcodes or RFID chips.

Alternatively, the individual treatment recommendation may include advising the individual to use hair care products which are individually produced for the individual and to initiate an ordering process, for example by calling up a website of a manufacturer of individual hair care products.

For example, the calibration model from b) exists as stored information on a local data carrier or in a cloud. As such, step c) may be carried out at a hairdressers, at a point of sale (POS) of hair treatment means or in the private domain.

Step c) may be controlled by a smart terminal such as, for example, a smart phone, a MILAN-enabled media player or a tablet, for example via a pre-installed app.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the various embodiments in any way. Rather, the foregoing detailed description will provide those skilled in the art with a convenient road map for implementing an exemplary embodiment as contemplated herein. It being understood that various changes may be made in the function and arrangement of elements described in an exemplary embodiment without departing from the scope of the various embodiments as set forth in the appended claims.

The invention claimed is:

1. A method for determining a degree of damage to hair utilizing a portable electronic device including an interference microscope and a data processing device, the method comprising the steps of:
utilizing the interference microscope of the portable electronic device, registering light radiated by the hair sample while the hair sample is illuminated with light;
evaluating the registered light utilizing the data processing device of the portable electronic device to determine first regions of the hair sample which reflect the light with higher interference and second regions of the hair sample which reflect the light with lower interference;
determining a degree of damage to the hair sample based on a size of the first regions of the hair sample in relation to the whole hair sample; and
outputting a product recommendation based on the determined degree of damage to the hair sample.

2. The method as claimed in claim 1, wherein the registration of the light further comprises recording a photograph of the hair sample.

3. The method as claimed in claim 2, wherein the step of evaluating the registered light includes evaluating the registered light to determine the first regions of the hair sample and to determine the second regions of the hair sample by determining brighter regions and darker regions of the photograph.

4. The method as claimed in claim 3, wherein the determination of the first regions of the hair sample comprises determining regions of the photograph with a brightness that is greater than or equal to a predetermined threshold.

5. The method as claimed in claim 4, wherein the determination of the second regions of the hair sample comprises the determination of regions of the photograph with a brightness that is less than or equal to the predetermined threshold.

6. The method as claimed in claim 1, comprising determining the degree of damage for a plurality of hair samples and determining, as the degree of damage to the hair, a mean degree of damage for the determined degrees of damage.

7. The method as claimed in claim 1, wherein the hair sample comprises one or more hairs.

8. The method as claimed in claim 1, wherein results from comparative measurements are used for the determination of the degree of damage to the hair.

9. The method as claimed in claim 1, wherein the degree of damage is determined on the basis of calibration data which represent a previously determined allocation of proportions from regions with higher interference in hair samples to degrees of damage.

10. The method as claimed in claim 9, comprising determining the calibration data based on hair samples with known damage.

11. The method as claimed in claim 10, comprising producing known damage in the hair samples by means of predetermined stretching of the hairs of the hair samples.

12. The method as claimed in claim 1, comprising illuminating the hair sample with white light.

13. A method for determining an individual hair treatment recommendation, comprising the steps of:
   a) recording interference patterns for a plurality of samples of hair which have been damaged to varying extents by stretching and relaxing the hair a varying number of stretching/relaxing cycles;
   b) establishing a calibration model which provides a correlation between the recorded interference patterns for the plurality of samples of hair which have been damaged and a degree of damage;
   c) recording interference patterns of hair from an individual;
   d) comparing the recorded interference patterns of the hair from the individual with the calibration model to determine the degree of damage to the hair of the individual; and
   e) outputting an individual recommendation regarding the treatment of the hair of the individual which is dependent upon the determined degree of damage.

14. The method as claimed in claim 13, wherein the step of recording the interference patterns of the hair from the individual is further defined as recording a photograph of a hair sample of the individual with the photograph including the interference patterns of the hair from the individual.

15. The method as claimed in claim 13, wherein the step of recording the interference patterns for the plurality of samples of hair which have been damaged is further defined as recording the interference patterns for the plurality of samples of hair which have been damaged to varying extents by stretching the hair about 20% and then relaxing the hair from about 1 second at room temperature a varying number of stretching/relaxing cycles.

16. The method as claimed in claim 13, wherein at least the steps of recording the interference patterns of hair from the individual, comparing the recorded interference patterns of the hair from the individual, and outputting the individual recommendation regarding the treatment of the hair of the individual are performed utilizing a portable electronic device including an interference microscope and a data processing device.

17. The method as claimed in claim 16, wherein the outputting step is performed automatically utilizing the data processing device of the portable electronic device.

* * * * *